(12) United States Patent
Tajima

(10) Patent No.: US 10,074,679 B2
(45) Date of Patent: Sep. 11, 2018

(54) RADIATION IMAGE DETECTING DEVICE

(71) Applicant: FUJIFILM Corporation, Tokyo (JP)

(72) Inventor: Takashi Tajima, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 658 days.

(21) Appl. No.: 14/606,764

(22) Filed: Jan. 27, 2015

(65) Prior Publication Data

US 2015/0164458 A1 Jun. 18, 2015

Related U.S. Application Data

(63) Continuation of application No. PCT/JP2013/073285, filed on Aug. 30, 2013.

(30) Foreign Application Priority Data

Sep. 4, 2012 (JP) .................... 2012-194581

(51) Int. Cl.
 *H05G 1/38* (2006.01)
 *H05G 1/44* (2006.01)
 (Continued)

(52) U.S. Cl.
 CPC ...... *H01L 27/14605* (2013.01); *A61B 6/4233* (2013.01); *H01L 27/14603* (2013.01);
 (Continued)

(58) Field of Classification Search
 CPC ....... A61B 6/42; A61B 6/4208; A61B 6/4233; A61B 6/4266; A61B 6/4283; H01L 27/1446; H01L 27/146; H01L 27/14601; H01L 27/14603; H01L 27/14605; H01L 27/14607; H01L 27/14609; H01L 27/14634; H01L 27/14658; H01L 27/14676; G01T 1/00; G01T 1/02; G01T 1/026; G01T 1/16; G01T 1/1603;
 (Continued)

(56) References Cited

U.S. PATENT DOCUMENTS 9,629,601 B2 *  4/2017  Tajima ............... A61B 6/542
2011/0180717 A1  7/2011  Okada
2013/0202086 A1  8/2013  Tsuji

FOREIGN PATENT DOCUMENTS

JP    2011-174908 A     9/2011
JP    2013-176544 A     9/2013
JP    WO 2013157475 A1 * 10/2013 ........... A61B 6/4208

OTHER PUBLICATIONS

International Search Report, issued in PCT/JP2013/073285, dated Oct. 29, 2013.

(Continued)

*Primary Examiner* — Anastasia Midkiff
(74) *Attorney, Agent, or Firm* — Birch, Stewart, Kolasch & Birch, LLP

(57) ABSTRACT

A sensor panel of an electric cassette is provided with detection pixels for AEC to stop X-ray irradiation when an accumulated dose of the X-rays reaches a target dose. A plurality of small blocks each containing a plurality of the detection pixels for calculating the accumulated dose are disposed in each of a plurality of large blocks obtained by dividing an imaging area. The small blocks are disposed so as not to be overlapped with each other in a Y direction.

4 Claims, 12 Drawing Sheets

(51) Int. Cl.
  *H01L 27/146* (2006.01)
  *G01T 1/16* (2006.01)
  *G01T 7/00* (2006.01)
  *H05G 1/28* (2006.01)
  *H04N 5/32* (2006.01)
  *A61B 6/00* (2006.01)

(52) U.S. Cl.
  CPC .. *H01L 27/14607* (2013.01); *H01L 27/14634* (2013.01); *H05G 1/38* (2013.01); *H05G 1/44* (2013.01); *A61B 6/4283* (2013.01); *A61B 6/542* (2013.01); *A61B 6/563* (2013.01); *G01T 1/1603* (2013.01); *G01T 7/005* (2013.01); *H04N 5/32* (2013.01); *H05G 1/28* (2013.01)

(58) Field of Classification Search
  CPC .. G01T 1/20; G01T 1/24; G01T 1/244; G01T 1/247; G01T 7/00; G01T 7/005; H05G 1/00; H05G 1/08; H05G 1/26; H05G 1/28; H05G 1/30; H05G 1/32; H05G 1/38; H05G 1/40; H05G 1/42; H05G 1/44; H05G 1/56
  See application file for complete search history.

(56) References Cited

OTHER PUBLICATIONS

Written Opinion of the International Searching Authority, issued in PCT/JP2013/073285, dated Oct. 29, 2013.

* cited by examiner

FIG.5

| BODY PART TO BE IMAGED | TUBE VOLTAGE (kV) | TUBE CURRENT (mA) | IRRADIATION STOP THRESHOLD VALUE |
|---|---|---|---|
| ... | ... | ... | ... |
| CHEST AP | V1 | I1 | th1 |
| CHEST PA | V2 | I2 | th2 |
| ... | ... | ... | ... |

70

RADIATION IMAGE DETECTING DEVICE

CROSS-REFERENCE TO RELATED APPLICATIONS

This application is a Continuation of PCT International Application No. PCT/JP2013/073285 filed on Aug. 30, 2013, which claims priority under 35 U.S.C. § 119(a) to Japanese Patent Application No. 2012-194581 filed Sep. 4, 2012. The above application is hereby expressly incorporated by reference, in its entirety, into the present application.

BACKGROUND OF THE INVENTION

1. Field of the Invention

The present invention relates to a radiation image detecting device for detecting a radiation image.

2. Description Related to the Prior Art

In a medical field, an X-ray imaging system using radiation such as X-rays is known. The X-ray imaging system includes an X-ray generating apparatus for generating X-rays and an X-ray imaging apparatus for acquiring an X-ray image of an object (i.e. patient) from the X-rays that have passed through the object. The X-ray generating apparatus includes an X-ray source for irradiating the X-rays to the object, a source controller for controlling the operation of the X-ray source, and an irradiation switch for inputting a command for actuating the X-ray source to the source controller. The X-ray imaging apparatus includes an X-ray image detecting device for detecting the X-ray image by converting the X-rays having passed through the object into an electrical signal, and a console for controlling the operation of the X-ray image detecting device and storing and displaying the X-ray image.

An X-ray imaging apparatus using an X-ray image detecting device for electronically detecting an X-ray image has been widely spread instead of an X-ray image recording device using an X-ray film or an imaging plate (IP) cassette. The X-ray image detecting device has a sensor panel that is also referred to as a flat panel detector (FPD). The sensor panel has an imaging area in which a plurality of pixels for accumulating signal charges corresponding to a dose of incident X-rays are arranged in a matrix. Each of the pixels has a photoelectric converter for generating electric charges and accumulating the generated electric charges, and a switching element such as a thin film transistor (TFT). The sensor panel reads out the signal charges accumulated in the photoelectric converter of each of the pixels through a signal line disposed for each column of the pixels in a signal processing circuit upon turning on of the switching element, and the signal charges are converted into a voltage signal in the signal processing circuit. Thereby, an X-ray image is electronically detected.

Further, in the X-ray imaging system, in order to suppress radiation exposure to the object and acquire an X-ray image with appropriate image quality, automatic exposure control (AEC) is performed in some cases. In the AEC, a dose detection sensor measures a dose of X-rays during the X-ray imaging (i.e. during X-ray irradiation), and the X-ray irradiation from an X-ray source is stopped when an integrated value of the dose (i.e. an accumulated dose) reaches a target dose. The dose of the X-rays irradiated from the X-ray source is determined by a tube current-time product (mAs value) which is the product of X-ray irradiation time (in units of seconds "s") and tube current (in units of milliamperes "mA") for defining the dose of the X-rays to be irradiated from the X-ray source per unit of time. Each of the imaging conditions such as the X-ray irradiation time and the tube current has a rough recommendation value depending on a body part to be imaged (chest, head, and the like), the sex, the age, and the like of the object. However, X-ray transmittance varies in accordance with the individual difference such as a body frame of the object, and therefore the AEC is performed to achieve more appropriate image quality.

An ion chamber or the like has been conventionally used as the dose detection sensor. However, recently, there has been proposed a technique that pixels of a sensor panel are subjected to simple modification so as to function as a dose detection sensor. In an X-ray image detecting device disclosed in United States Patent Application Publication No. 2011/0180717 (corresponding to Japanese Patent Laid-Open Publication No. 2011-174908), some of pixels (hereinafter referred to as detection pixels) are each connected without intermediation of a switching element to a radiation detection line, and a dose signal corresponding to the electric charges generated in each of the detection pixels flow into the radiation detection line irrespective of whether the switching element is turned on or turned off. Then, the dose signal is sampled in an AEC section to which the radiation detection line is connected, and an integrated value of the sampled dose signals is calculated. Based on the calculated integrated value, it is determined whether or not the accumulated dose has reached the target dose.

As shown in FIG. 12, according to United States Patent Application Publication No. 2011/0180717, among pixels 200 arranged in 4-by-4 matrix, for example, the pixel in the first row and the second column, the pixel in the second row and the first column, the pixel in the third row and the third column, and the pixel in the fourth row and the fourth column are specified as detection pixels 200*b* (shown by hatching). Thus, the detection pixels 200*b* are dispersedly arranged such that the detection pixel 200*b* is disposed one-by-one in each row and each column. Further, in order to increase a level of the dose signal for the purpose of improving the decision accuracy in the AEC, the two detection pixels 200*b* including the pixel 200*b* in the first row and the second column and the pixel 200*b* in the second row and the first column are connected to a first radiation detection line 201*a*, and the two detection pixels 200*b* including the pixel 200*b* in the third row and the third column and the pixel 200*b* in the fourth row and the fourth column are connected to a second radiation detection line 201*b*, respectively, such that the dose signals from the former two pixels 200*b* and the dose signals from the latter two pixels 200*b* are added up and inputted to an AEC section 202.

The AEC section 202 integrates the additional value of the dose signals from the former two pixels 200*b* and the dose signals from the latter two pixels 200*b* at each sampling of the dose signals, and determines whether or not the accumulated dose has reached the target dose based on the integrated value. Namely, the integrated value of the additional values of the dose signals from the former two pixels 200*b* and the dose signals from the latter two pixels 200*b* is calculated as the accumulated dose for blocks 203*a* and 203*b* each of which consists of two rows and two columns and is shown by a thick frame in FIG. 12.

According to United States Patent Application Publication No. 2011/0180717, since a block 203*c* on the right of the block 203*a* and a block 203*d* on the left of the block 203*b* do not include the detection pixels 200*b*, it is impossible to obtain data of an accumulated dose in each of the blocks 203c and 203d. Therefore, the determination accuracy of the AEC section 202 is also decreased.

SUMMARY OF THE INVENTION

In view of the foregoing, an object of the present invention is to provide a radiation image detecting device capable of obtaining more accurate information of accumulated dose of radiation and performing AEC more correctly.

To achieve the above and other objects of the present invention, a radiation image detecting device of the present invention includes a sensor panel having an imaging area provided with pixels each for accumulating electric charges corresponding to a dose of radiation having passed through an object and outputting the accumulated electric charges to a signal line. In the sensor panel, part of the pixels are used as detection pixels for detecting the radiation dose. The radiation image detecting device performs automatic exposure control, in which it is determined whether or not an accumulated dose has reached a target dose based on output of the detection pixels through the signal lines, and radiation irradiation is stopped when it is determined that the accumulated dose has reached the target dose. The sensor panel has a plurality of large blocks obtained by dividing the imaging area in a first direction along the signal lines and a second direction orthogonal to the first direction, and at least one small block disposed in each of the large blocks. The small block consists of a plurality of the detection pixels connected to a single one of the signal lines. The small blocks are arranged so as not to be overlapped with each other in the first direction.

An arrangement pattern of the small blocks is the same in each of the large blocks, for example. In this case, the arrangement pattern of the small blocks is deviated between the large blocks adjacent to each other in the first direction with a deviation degree corresponding to at least one of the signal lines in the first direction.

The detection pixels are arranged densely in a particular portion in the large block, for example. The particular portion is a central portion of the large block, for example. The detection pixels may be arranged so as to be evenly dispersed in the large block.

The detection pixels are aligned in the second direction, for example.

The small blocks may be arranged in the large block so as to be sequentially shifted from each other in the second direction along a diagonal line of the large block.

The small block is disposed so as not to straddle the large blocks adjacent to each other.

The pixels include the detection pixels and normal pixels different from the detection pixels. Each of the normal pixels accumulates the electric charges and outputs the electric charges to the signal line upon turning off and on of a first switching element. The electric charges generated in each of the detection pixels flow into the signal line irrespective of whether the first switching element is turned on or turned off. In this case, the small blocks are arranged with an interval corresponding to at least one of the signal lines therebetween, such that the signal line not being provided with the small blocks is adjacent to the signal line being provided with the small blocks. The radiation image detecting device further includes a subtraction device for subtracting a voltage signal outputted from the signal line not being provided with the small blocks in a state that the first switching element is turned off from a voltage signal outputted from the signal line being provided with the small blocks in a state that the first switching element is turned off.

The automatic exposure control is preferably performed based on the voltage signal obtained by the subtraction by the subtraction device.

The subtraction device preferably samples the voltage signals outputted from a plurality of the signal lines each of which is not provided with the small blocks.

The pixels include the detection pixels and normal pixels different from the detection pixels. Each of the normal pixels accumulates the electric charges and outputs the electric charges to the signal line upon turning off and on of a first switching element. Each of the detection pixels is provided with a second switching element in addition to the first switching element. The electric charges generated in each of the detection pixels flow into the signal line upon turning on of the second switching element irrespective of whether the first switching element is turned on or turned off. In this case, the radiation image detecting device further includes a subtraction device for subtracting a voltage signal outputted from the signal line being provided with the small blocks in a state that the first and second switching elements are turned off from a voltage signal outputted from the same signal line in a state that the first switching element is turned off and the second switching element is turned on. The automatic exposure control is preferably performed based on the voltage signal obtained by the subtraction by the subtraction device.

The detection pixels are arranged with an interval of at least one pixel therebetween in the first direction. The large block may have either a square shape or a rectangular shape.

It is preferable that the sensor panel is a portable electric cassette contained in a housing.

According to the present invention, at least one small block, in which a plurality of the detection pixels for detecting the radiation dose for the automatic exposure control are connected to a single one of the signal lines, is disposed in each of a plurality of the large blocks obtained by dividing the imaging area in the first direction along the signal lines and the second direction orthogonal to the first direction. In the case where the number of the small blocks is two or more, the small blocks are disposed so as not to be overlapped with each other in the first direction. Consequently, it is possible to obtain more accurate information of the accumulated dose of radiation, and perform the AEC more correctly.

BRIEF DESCRIPTION OF DRAWINGS

For more complete understanding of the present invention, and the advantage thereof, reference is now made to the subsequent descriptions taken in conjunction with the accompanying drawings, in which:

FIG. 5 is a table showing imaging conditions;

DESCRIPTION OF THE PREFERRED EMBODIMENTS

Figure 1:
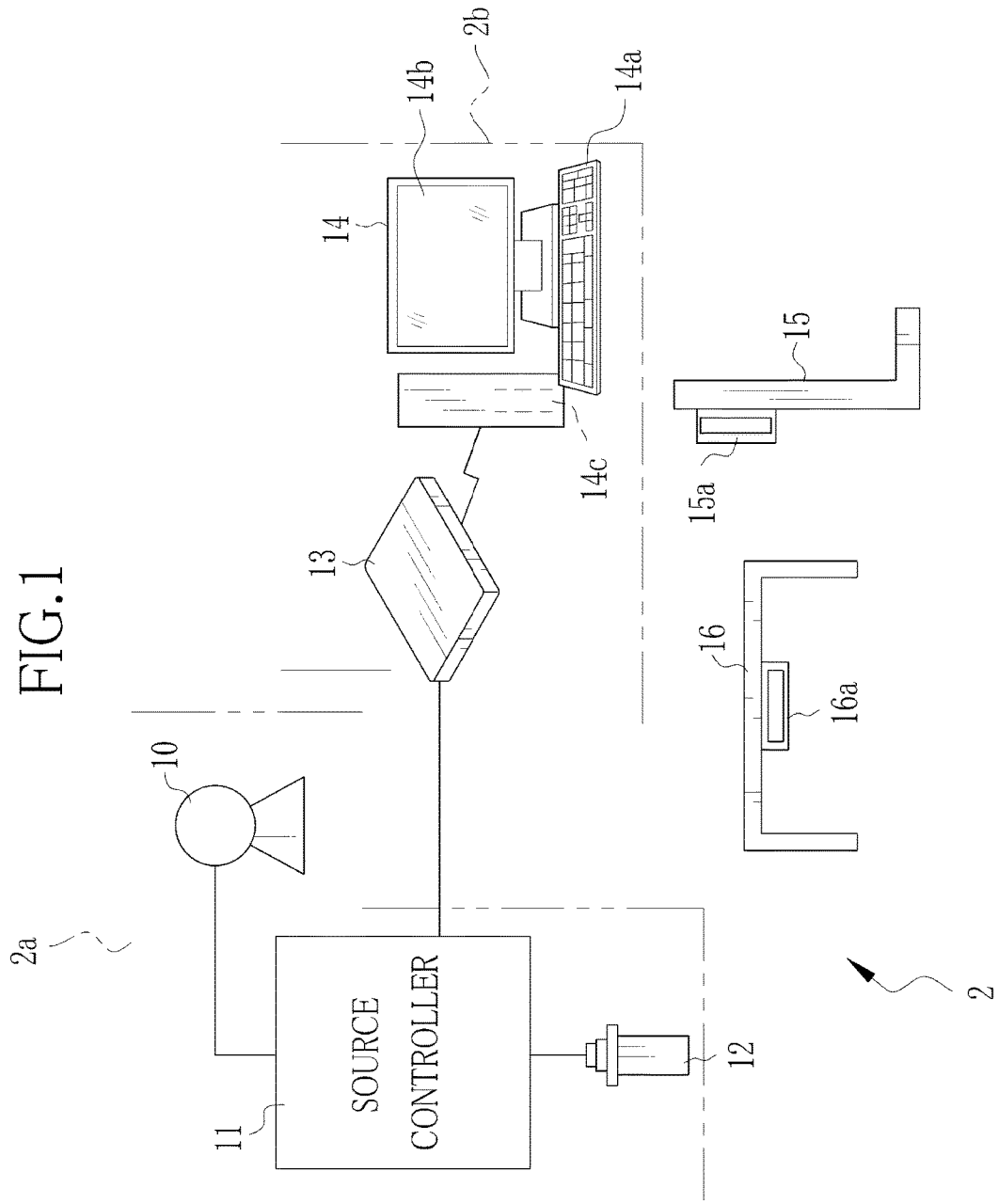
FIG. 1 is a schematic view showing an X-ray imaging system.

In FIG. 1, an X-ray imaging system 2 of the present invention includes an X-ray source 10, a source controller 11 for controlling operation of the X-ray source 10, an irradiation switch 12 for giving a command to start warming-up and X-ray irradiation to the X-ray source 10, an electronic cassette 13 for detecting X-rays having passed through an object (i.e. patient) and outputting an X-ray image, a console 14 for performing operation control of the electronic cassette 13 and display processing of X-ray images, an upright-posture imaging table 15 for imaging the object in a standing posture, and a supine-posture imaging table 16 for imaging the object in a lying posture. The X-ray source 10, the source controller 11, and the irradiation switch 12 constitute an X-ray generating apparatus 2a. The electronic cassette 13 and the console 14 constitute an X-ray imaging apparatus 2b. Additionally, a source moving device (not shown in the drawing) is provided to set the X-ray source 10 in a desired direction and at a desired position. The X-ray source 10 is shared between the upright-posture imaging table 15 and the supine-posture imaging table 16.

The X-ray source 10 has an X-ray tube and an irradiation field limiter (collimator) for limiting an irradiation field of the X-rays to be irradiated from the X-ray tube. The X-ray tube has a cathode composed of a filament for emitting thermal electrons, and an anode (target) for irradiating the X-rays upon collision with the thermal electrons emitted from the cathode. Upon receiving a command to start the warming-up of the X-ray source 10, the anode starts rotating. After the anode rotates by the prescribed number of rotations, the warming-up of the X-ray source 10 is finished. The irradiation field limiter is composed of, for example, four lead plates for shielding the X-rays disposed on each side of a quadrangle, such that a quadrangular irradiation opening through which the X-rays pass is formed in the middle thereof. Shifting of the positions of the lead plates varies the size of the irradiation opening so as to limit the irradiation field.

The console 14 is communicably connected to the electronic cassette 13 in a wired manner or a wireless manner, and controls the operation of the electronic cassette 13 in response to input operation by an operator through an input device 14a such as a keyboard. The X-ray image transmitted from the electronic cassette 13 is displayed on the monitor 14b of the console 14, and further, the data thereof is stored in a data storage. The data storage is, for example, a storage device 14c such as a hard disk or a memory in the console 14, or an image storage server connected to the console 14 through a network.

The console 14 receives the input of an examination order containing information relating to the sex, age, body part to be imaged, and imaging objective of each object, and displays the examination order on the monitor 14b. The examination order is inputted from an external system, such as hospital information system (HIS) or radiation information system (RIS), which manages patient information and examination information relating to radiographic examination. Alternatively, the examination order is inputted manually by an operator such as a radiation technologist. Items regarding the body part to be imaged such as head, chest, abdomen, hand, and finger are contained in the examination order. Additionally, the body part to be imaged includes an imaging direction such as front, side, oblique, PA (in which X-rays are irradiated from the rear of the object), and AP (in which X-rays are irradiated from the front of the object). The operator confirms the details of the examination order on the monitor 14b, and inputs the imaging condition corresponding to the details through the operation screen displayed on the monitor 14b using the input device 14a.

The imaging conditions include, in addition to the body part to be imaged, tube voltage (unit; kV) for determining energy spectrum of the X-rays to be irradiated from the X-ray source 10, tube current (unit; mA) for determining a dose of the X-rays per unit of time, an irradiation time (unit; s) of the X-rays, and the like. The accumulated dose of the X-rays is defined by the product of the tube current and the irradiation time. With regard to the imaging condition, instead of inputting the value of tube current and the value of irradiation time separately, the value of tube current-time product (mAs value) as the product of them is inputted in some cases.

Figure 2:
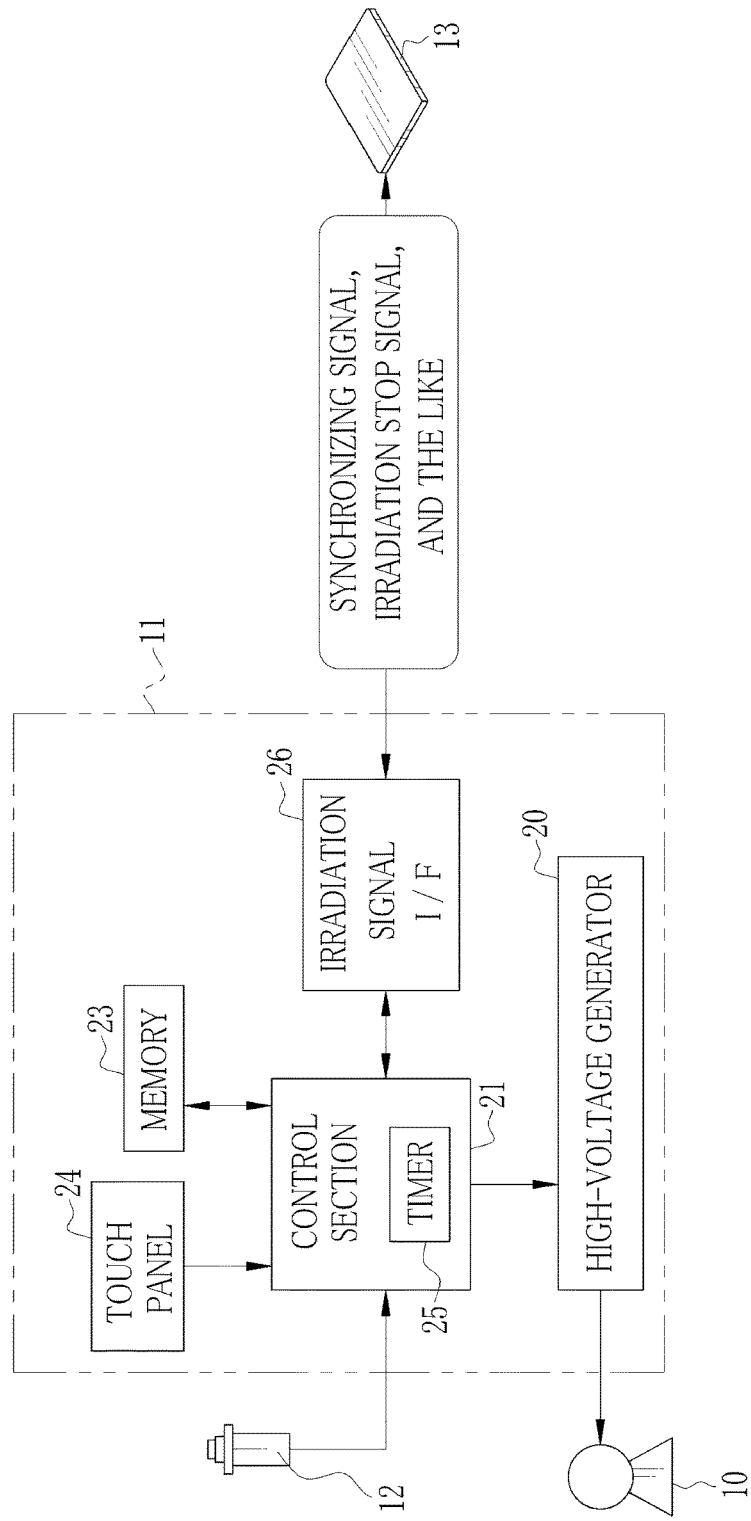
FIG. 2 is a view showing an internal structure of a source controller.

As shown in FIG. 2, the source controller 11 includes a high-voltage generator 20, a control section 21, a memory 23, a touch panel 24, and an irradiation signal I/F 26. The high-voltage generator 20 generates a high tube voltage by multiplying an input voltage using a transformer, and supplies the X-ray source 10 with the high tube voltage through a high-voltage cable. The control section 21 controls the tube voltage and the tube current to be supplied to the X-ray source 10, and the irradiation time of the X-rays. The irradiation signal I/F 26 mediates transmission and reception of signals to and from the electronic cassette 13.

The irradiation switch 12, the memory 23, and the touch panel 24 are connected to the control section 21. The irradiation switch 12 is a two-step push-button switch for inputting a command for actuating the control section 21. Upon first-step pressing (i.e. halfway pressing) of the irradiation switch 12, the control section 21 issues a warm-up start signal to the high-voltage generator 20 so as to start the warming-up of the X-ray source 10. Upon second-step pressing (i.e. full pressing) of the irradiation switch 12, the control section 21 transmits and receives a synchronizing signal to and from the electronic cassette 13 so as to achieve synchronization control, and then issues an irradiation start signal to the high-voltage generator 20 so as to start the X-ray irradiation from the X-ray source 10.

The memory 23 stores in advance several types of imaging conditions including the tube voltage, the tube current, the irradiation time, and the like. The imaging condition is set manually by the operator through the touch panel 24. A plurality types of imaging conditions read out from the memory 23 are displayed on the touch panel 24. The operator selects the same imaging condition as that inputted to the console 14 from among the imaging conditions displayed on the touch panel 24, so as to set the imaging condition for the source controller 11. As a matter of course, it is also possible to perform fine adjustment of the values of the imaging conditions preliminarily prepared. The control section 21 incorporates a timer 25 used for stopping the X-ray irradiation when the set irradiation time has elapsed. Note that, the imaging condition for the source controller 11 may be automatically set by transmitting the imaging condition inputted to the console 14 to the source controller 11.

In order to prevent a shortage of the X-ray dose because of the reason that the X-ray irradiation is stopped before the accumulated dose has reached the target dose and a decision to stop the X-ray irradiation is made in the AEC, the irradiation time with a margin is set in the case where the AEC is performed. The maximum value of the irradiation time set in accordance with safety regulations in the X-ray source 10 also may be used. In the case where the AEC is not performed, the irradiation time is set in accordance with the body part to be imaged. The control section 21 controls the X-ray irradiation based on the tube voltage, the tube current, and the irradiation time set in the imaging condition. In the case where it is determined that the accumulated dose of the X-rays has reached a necessary and sufficient target dose, the AEC functions to stop the X-ray irradiation even before the irradiation time preliminarily set in the source controller 11 is not achieved. Note that, in the case where the AEC is performed and the irradiation time is set to the maximum value, the irradiation time is preferably set in accordance with the body part to be imaged.

The irradiation signal I/F 26 mediates transmission and reception of the synchronizing signal in the synchronization control performed between the source controller 11 and the electronic cassette 13. The control section 21 transmits an irradiation start request signal, which is a synchronizing signal for inquiring whether or not to permit the start of X-ray irradiation, to the electronic cassette 13 before the start of X-ray irradiation. In response to the irradiation start request signal, the control section 21 receives from the electronic cassette 13 an irradiation permission signal which is a synchronizing signal for indicating that the preparation for receiving the X-ray irradiation has been completed. Further, the irradiation signal I/F 26 receives an irradiation stop signal from the electronic cassette 13 when the electronic cassette 13 performs the AEC. The communication system of the irradiation signal I/F 26 may be in a wired manner or in a wireless manner.

Figure 3:
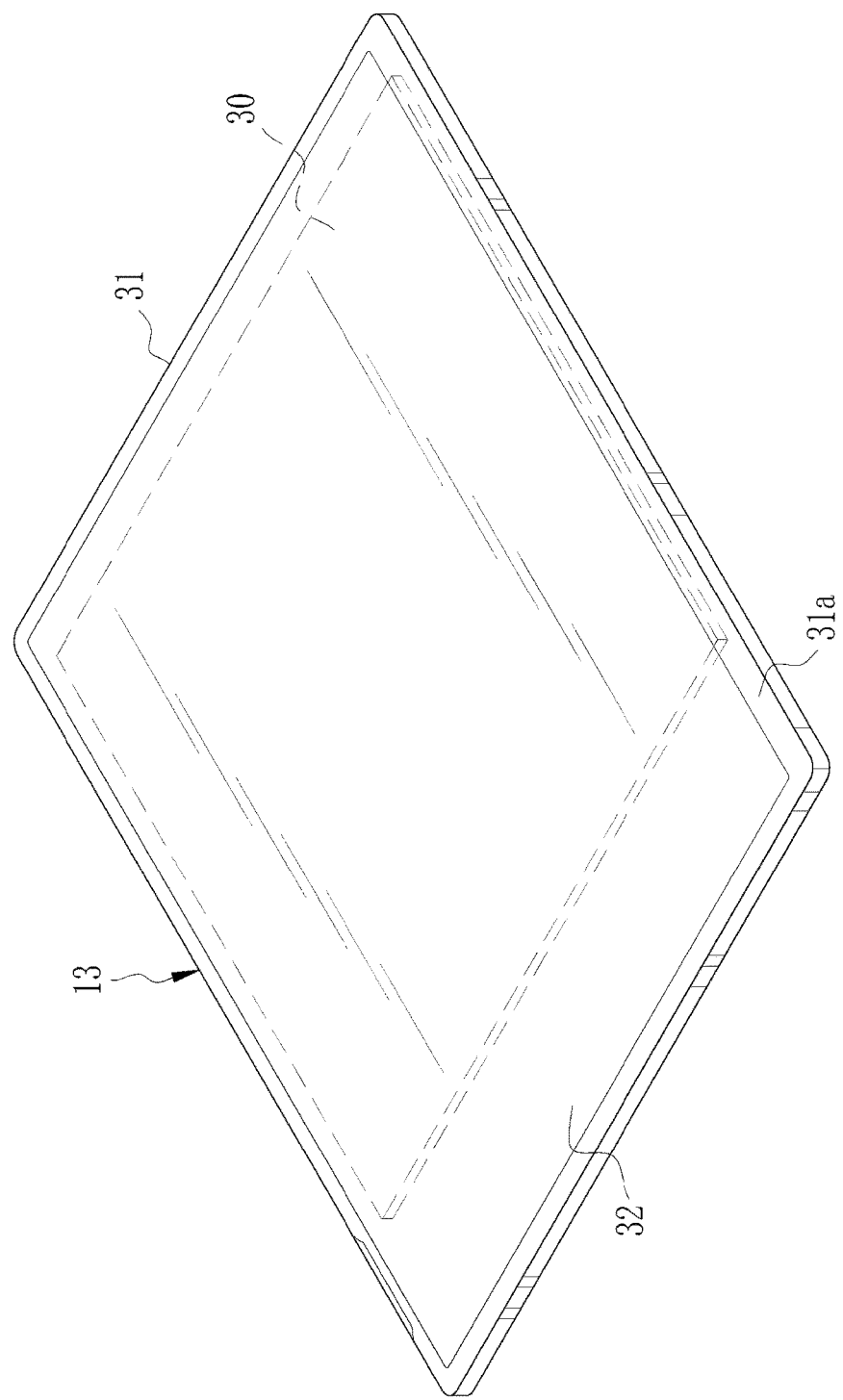
FIG. 3 is a perspective view showing an external appearance of an electronic cassette.

In FIG. 3, the electronic cassette 13 consists of a sensor panel 30 and a flat box-shaped portable housing 31 for containing the sensor panel 30. The housing 31 is formed from a conductive resin, for example. A front surface 31a of the housing 31, through which the X-rays enter, has an opening in a rectangular shape. A transparent plate 32 as a top panel is attached to the opening. The transparent plate 32 is formed from a carbon material that is lightweight and has high rigidity and high X-ray transparency. The housing 31 also functions as an electromagnetic shield for preventing electromagnetic noise from entering the electronic cassette 13 and for preventing electromagnetic noise from being emitted from the electronic cassette 13 to the outside. Note that, the housing 31 incorporates not only the sensor panel 30 but also a battery (secondary battery) for supplying electricity at a predetermined voltage to the respective components of the electronic cassette 13 and an antenna for use in wireless communication of data such as X-ray image with the console 14.

The housing 31 has approximately the same size as those of a film cassette and an IP cassette. The size of the housing 31 is compatible with International Standard ISO 4090: 2001. Therefore, the electronic cassette 13 is detachably set to holders 15a and 16b of the imaging tables 15 and 16 (see FIG. 1), respectively, such that the front surface 31a of the housing 31 is held in a posture facing the X-ray source 10. Then, the X-ray source 10 is moved by the source moving device depending on the imaging table to be used. Further, in some cases, the electronic cassette 13 is put on a bed on which the object is lying, or held by the object itself, to be used solely, in stead of being set to the imaging table 15 or 16. Note that, the electronic cassette 13 has approximately the same size as those of the film cassette and the IP cassette, and therefore the electronic cassette 13 can be attached to an existing imaging table designed for the film cassette and the IP cassette.

Figure 4:
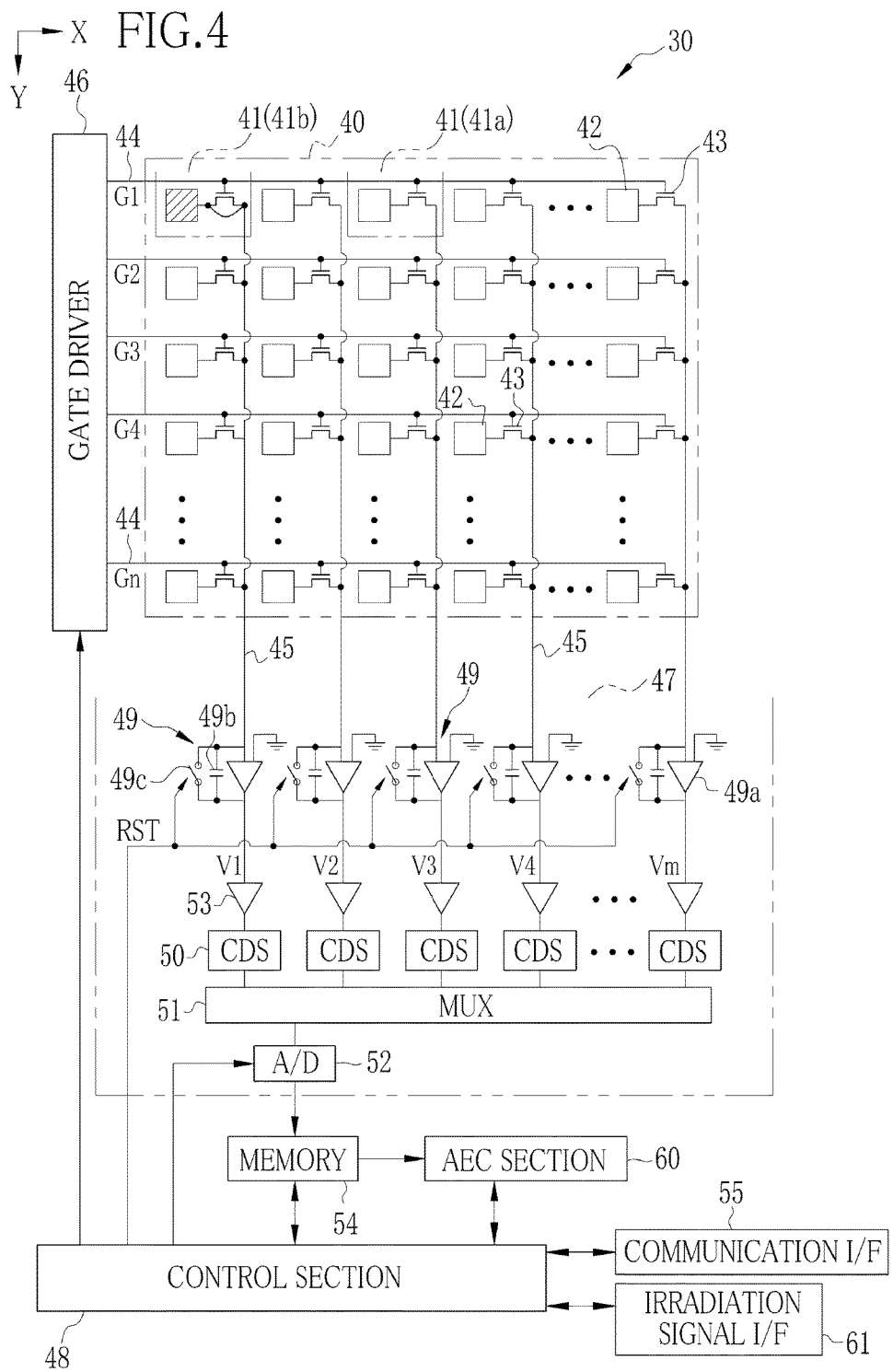
FIG. 4 is a block diagram showing an internal structure of the electronic cassette.

In FIG. 4, the sensor panel 30 has a TFT active matrix substrate on which an imaging area 40 is formed. On the imaging area 40, a plurality of pixels 41 for accumulating electric charges corresponding to the received X-ray dose are arranged into a matrix form with n rows (that is X direction or second direction) and m columns (that is Y direction or first direction) at a predetermined pitch. Note that, each of n and m is an integer of two or more.

The sensor panel 30 has a scintillator (i.e. a phosphor, not shown in the drawing) for converting X-rays into visible light. The sensor panel 30 is of an indirect-conversion type in which visible light obtained by being converted by the scintillator is photoelectrically converted in the pixels 41. The scintillator is made of CsI:Tl (thallium activated cesium iodide), GOS ($Gd_2O_2S$:Tb, terbium activated gadolinium oxysulfide), or the like, and is opposed to the entire surface of the imaging area 40 on which the pixels 41 are arranged. Note that, the scintillator and the TFT active matrix substrate may be disposed according to either a Penetration Side Sampling (PSS) system in which the scintillator and the substrate are disposed in this order from the X-ray incident side, or an irradiation side sampling (ISS) system in which the substrate and the scintillator are disposed in this order from the X-ray incident side, in contrast to the PSS system. Alternatively, a sensor panel of a direct-conversion type, which has a conversion layer (amorphous selenium or the like) for directly converting the X-rays into the electric charges without using the scintillator, may be used instead.

As well known, each of the pixels 41 includes a photoelectric converter 42 for generating the electric charges (electron-hole pairs) upon incidence of the visible light and accumulating the generated electric charges, and a TFT 43 as a switching element. Note that, a capacitor for accumulating the electric charges may be provided separately from the photoelectric converter 42.

Each of the photoelectric converter 42 has a structure in which a semiconductor layer (for example, of a PIN (p-intrinsic-n) type) for generating electric charges is sandwiched between an upper electrode and a lower electrode. In each of the photoelectric converters 42, the TFT 43 is connected the lower electrode, and a bias line is connected to the upper electrode. The number of the bias lines corresponds to the number of rows (n rows) of the pixels 41, and the bias lines are coupled to a single bus. The bus is connected to a bias power supply. A bias voltage is applied from the bias power supply to the upper electrode of each of the photoelectric converters 42 through the bus and the bias line as a subordinate of the bus. With the application of the bias voltage, an electric field is generated in the semiconductor layer, and the electric charges (electron-hole pairs) generated in the semiconductor layer by photoelectric conversion are moved to the upper electrode and the lower electrode, one of which has positive polarity, and the other of which has negative polarity. Thereby, the electric charges are accumulated in the photoelectric converters 42.

Each of the TFTs 43 has a gate electrode connected to a scanning line 44, a source electrode connected to a signal line 45, and a drain electrode connected to the photoelectric converter 42. The scanning lines 44 and the signal lines 45 are wired in a lattice shape along the X and Y directions. The number of the scanning lines 44 corresponds to the number of rows (n rows) of the pixels 41, such that one scanning line 44 is provided for the pixels 41 arranged in one row. Further, the number of the signal lines 45 corresponds to the number of columns (m columns) of the pixels 41, such that one signal line 45 is provided for the pixels 41 arranged in one column. The scanning lines 44 are connected to a gate driver 46, and the signal lines 45 are connected to a signal processing circuit 47.

Under the control of a control section 48, the gate driver 46 drives the TFTs 43, such that the sensor panel 30 carries out an accumulation operation for accumulating the signal charges corresponding to the received X-ray dose in the pixels 41, a readout operation for reading out the signal charges accumulated in the pixels 41, and a reset operation. In the accumulation operation, the signal charges are accumulated in the pixels 41 while the TFTs 43 are turned off. In the readout operation, the gate driver 46 sequentially issues gate pulses G1 to Gn, each of which drives the TFTs 43 in the same row at a time, at a predetermined time interval. Thereby, the scanning lines 44 are activated sequentially on a row-by-row basis, such that the TFTs 43 connected to the activated scanning lines 44 are turned on sequentially on a row-by-row basis. When the TFT 43 is turned on, the electric charges accumulated in the photoelectric converter 42 of the pixel 41 are read out to the signal line 45, and inputted to the signal processing circuit 47.

Dark charges are generated in the semiconductor layer of each of the photoelectric converters 42 irrespective of incidence of the X-rays. Due to the application of the bias voltage, the dark charges are accumulated in each of the photoelectric converters 42. The dark charges generated in the pixels 41 become noise components in the image data, and therefore the reset operation is carried out at a predetermined time interval so as to remove the dark charges before the start of the X-ray irradiation. The reset operation is carried out to discharge the dark charges generated in the pixels 41 through the signal lines 45.

The reset operation is carried out by a sequential reset method, for example, by which the pixels 41 are reset on a row-by-row basis. In the sequential reset method, as with the readout operation of the signal charges, the gate driver 46 sequentially issues the gate pulses G1 to Gn to the scanning lines 44 at a predetermined time interval so as to turn on the TFTs 43 on a row-by-row basis.

Instead of the sequential reset method, a parallel reset method or a all-pixels reset method may be used. In the parallel reset method, a plurality of rows of pixels are grouped together, and the reset operation is sequentially carried out in each of the groups, so as to concurrently discharge the dark charges from the rows corresponding to the number of the groups. In the all-pixels reset method, the gate pulse is inputted to every row to discharge the dark charges from every pixel at a time. The parallel reset method and the all-pixels reset method allow the speeding up of the reset operation.

The signal processing circuit 47 includes integration amplifiers 49, correlated double sampling (CDS) circuits 50, a multiplexer (MUX) 51, an A/D converter (A/D) 52, and the like. The integration amplifier 49 is connected one-by-one to each of the signal lines 45. Each of the integration amplifiers 49 consists of an operational amplifier 49a and a capacitor 49b connected between input and output terminals of the operational amplifier 49a. The signal line 45 is connected to one of input terminals of the operational amplifier 49a. The other input terminal of the operational amplifier 49a is connected to a ground (GND). To the capacitor 49b, a reset switch 49c is connected in parallel. Each of the integration amplifiers 49 integrates the electric charges inputted through the signal line 45, converts the electric charges into analog voltage signals V1 to Vm, and outputs the analog voltage signals V1 to Vm. An output terminal of the operational amplifier 49a in each column is connected to the MUX 51 through an amplifier 53 and the CDS circuit 50. The A/D 52 is connected to the output side of the MUX 51.

The CDS circuit 50, each having a sample-and-hold circuit, applies correlated double sampling to the output voltage signal from the integration amplifier 49 to remove the noise components, and holds the output voltage signal from the integration amplifier 49 for a predetermined period of time in the sample-and-hold circuit (i.e. performs sample holding). The MUX 51 sequentially selects one of the CDS circuits 50 connected in parallel from every row by using an electronic switch based on an operation control signal from a shift resister (not shown in the drawing), such that the voltage signals V1 to Vm outputted from the selected CDS circuits 50 are serially inputted to the A/D 52. Further, another amplifier may be connected between the MUX 51 and the A/D 52.

The A/D 52 converts the inputted analog voltage signals V1 to Vm corresponding to one row into a digital value, and outputs the digital value to a memory 54 contained in the electronic cassette 13. The memory 54 stores the digital value corresponding to one row in association with coordinates of each of the pixels 41 as image data of the X-ray image corresponding to one row. Thereby, the readout operation corresponding to one row is completed.

After the MUX 51 reads out the voltage signals V1 to Vm corresponding to one row from the integration amplifiers 49, the control section 48 outputs a reset pulse RST to the integration amplifiers 49, such that the reset switches 49c are turned on. Thereby, the signal charges accumulated in the capacitors 49b corresponding to one row are discharged, and the integration amplifiers 49 are reset. After the resetting of the integration amplifiers 49, the reset switches 49c are turned off again. After a lapse of a predetermined period of time from the turning off of the reset switches 49c, one of the sample-and-hold circuits in each of the CDS circuits 50 is held so as to sample a kTC noise component of the integration amplifier 49. Thereafter, the gate pulse corresponding to the next row is outputted from the gate driver 46 to start reading out the signal charges from the pixels 41 of the next row. After a lapse of a predetermined period of time from the outputting of the gate pulse, the signal charges of the pixels 41 corresponding to the next row are held by another one of the sample-and-hold circuits in each of the CDS circuits 50. By repetition of the above operation, the signal charges are read out from the pixels 41 corresponding to every row.

After the completion of the readout operation from every row, the image data representing the X-ray image of a single frame is stored in the memory 54. The image data is read out from the memory 54, and subjected to various types of image processing in the control section 48. Then, the image data is outputted to the console 14 through a communication I/F 55. Thereby, the X-ray image of the object is detected.

Note that, in the reset operation, while the TFTs 43 are turned on, the dark charges from the pixels 41 flow into the capacitors 49b of the integration amplifiers 49 through the signal lines 45. In contrast to the readout operation, the MUX 51 does not read out the electric charges accumulated in the capacitors 49b. In synchronization with the issue of each of the gate pulses G1 to Gn, the control section 48 outputs the reset pulse RST. Thereby, the reset switch 49*c* is turned on, and the electric charges accumulated in the capacitor 49*b* are discharged to reset the integration amplifier 49.

The control section 48 has circuits (not shown in the drawing) for applying the various types of image processing such as offset correction, sensitivity correction, and defect correction to the X-ray image data stored in the memory 54. The offset correction circuit subtracts an offset correction image, which is obtained from the sensor panel 30 without irradiation of the X-rays, from the X-ray image on a pixel-by-pixel basis, in order to remove fixed pattern noise caused by the individual difference of the signal processing circuit 47 and imaging environment. The sensitivity correction circuit, which is also called as a gain correction circuit, corrects variations in the sensitivity of the photoelectric converter 42 of each of the pixels 41, variations in the output property of the signal processing circuit 47, and the like. The defect correction circuit performs linear interpolation of a pixel value of a defect pixel using a pixel value of a normal pixel around the defect pixel, based on information of the defect pixel produced at the time of shipping or periodic inspection. The defect correction circuit also interpolates a pixel value of the detection pixel 41*b*. The console 14 may have the various image processing circuits as described above, so as to perform the various types of image processing.

The pixels 41 include normal pixels 41*a* and the detection pixels 41*b*. The normal pixels 41*a* are used to produce the X-ray image. Each of the detection pixels 41*b*, on the other hand, functions as a dose detection sensor for detecting the X-ray dose received by the imaging area 40. Each of the detection pixels 41*b* is used to stop the X-ray irradiation from the X-ray source 10 through the AEC function when the accumulated X-ray dose has reached the target dose. The positions of the detection pixels 41*b* are already known at the time of manufacturing the sensor panel 30, and the sensor panel 30 has a nonvolatile memory (not shown in the drawing) for storing the position (coordinates) of every detection pixel 41*b* in advance. Note that, in the drawing, the detection pixels 41*b* are hatched so as to be distinguished from the normal pixels 41*a*.

The basic structure including the photoelectric converter 42 and the like is exactly the same between the normal pixel 41*a* and the detection pixel 41*b*. Thus, the normal pixel 41*a* and the detection pixel 41*b* can be formed by almost the same manufacturing process. The TFT 43 of each of the detection pixels 41 has a short between the source electrode and the drain electrode. Therefore, the electric charges generated in the photoelectric converter 42 of each of the detection pixels 41*b* flow into the signal line 45 irrespective of whether the TFT 43 is turned on or turned off, and the TFTs 43 of the normal pixels 41*a* in the same row are turned off. Thereby, it is possible to read out the electric charges even while the accumulation operation for accumulating the signal charges is performed.

The electric charges generated in the photoelectric converter 42 of each of the detection pixels 41*b* flow into the capacitor 49*b* of the integration amplifier 49 through the signal line 45. The electric charges accumulated in the integration amplifier 49 is outputted from the detection pixel 41*b* to the A/D 52, and converted into a digital voltage signal (hereinafter referred to as a dose signal) by the A/D 52. The dose signal is outputted to the memory 54. The dose signal is stored in the memory 54 in association with the coordinate information of each of the detection pixels 41*b* in the imaging area 40. The sensor panel 30 repeats such a dose detection operation for several times at a predetermined sampling rate. Note that, in the case where the body of the object is thick, a level of the dose signal per unit time becomes low, and therefore the sampling rate may be made longer. In contrast, in the case where the body of the object is thin, the sampling rate may be made shorter.

The operation of an AEC section 60 is controlled by the control section 48. The AEC section 60 reads out the dose signals obtained at a predetermined sampling rate several times from the memory 54, and performs the AEC based on the dose signals thus read out.

The AEC section 60 sequentially adds up the dose signals read out from the memory 54 by the dose detection operation performed several times for each of the coordinates, so as to measure the accumulated dose of X-rays reaching the imaging area 40. More specifically, the AEC section 60 obtains the accumulated dose for each large block 75 (see FIG. 6) into which the imaging area 40 is equally divided in X and Y directions. The accumulated dose in each of the large blocks 75 is obtained as follows, for example. At first, an integrated value of the dose signals of a plurality of the detection pixels 41*b* constituting each small block 76 in each of the large blocks 75 is obtained. Then, the integrated value is divided by the number of the detection pixels 41*b* constituting each of the small blocks 76 to acquire an average value for each of the small blocks 76. Further, the average values are added up for each of the large blocks 75, and then the resultant value is divided by the number of the small blocks 76 contained in each of the large blocks 75, so as to acquire an average value. The acquired average value is used as the accumulated dose of each of the large blocks 75. The AEC section 60 defines one of the large blocks 75, which has the lowest accumulated dose among the large blocks 75, for example, as a dose measurement field that is a target field for the AEC.

Note that, the above-described method for determining the dose measurement field is shown as one example. The dose measurement field may be determined in accordance with the body part to be imaged. Alternatively, an arbitrary field may be defined as the dose measurement field by user settings. Further, the accumulated dose of each of the large blocks 75 is not necessarily the average value, and may be a total value of the integrated values of the dose signals of each of the small blocks 76 in each of the large blocks 75, the maximum value among the integrated values, or a mode value.

The AEC section 60 compares the accumulated dose of the large block 75 defined as the dose measurement field with a preliminarily-set irradiation stop threshold value (target dose), so as to determine whether or not the accumulated dose has reached the irradiation stop threshold value. When it is determined that the accumulated dose in the dose measurement field has exceeded the irradiation stop threshold value and the accumulated dose of the X-rays has reached the target dose, the AEC section 60 outputs the irradiation stop signal to the control section 48.

The irradiation signal I/F 26 of the source controller 11 is connected to an irradiation signal I/F 61 in a wired or wireless manner. The irradiation signal I/F 61 mediates transmission and reception of the synchronizing signal to and from the source controller 11 in the synchronization control. Specifically, the irradiation signal I/F 61 mediates reception of the irradiation start request signal from the source controller 11, and transmission of the irradiation permission signal in response to the irradiation start request signal to the source controller 11. Additionally, the irradiation signal I/F 61 receives the irradiation stop signal outputted from the AEC section 60 through the control section 48, and transmits the irradiation stop signal to the source controller 11.

The communication I/F 55 is connected to the console 14 in a wired or wireless manner, and mediates transmission and reception of information to and from the console 14. The communication I/F 55 receives the imaging condition inputted by an operator from the console 14, and inputs the data regarding the imaging condition to the control section 48.

The storage device 14c of the console 14 stores an imaging condition table 70 in which a plurality of imaging conditions are recorded in advance as shown in FIG. 5. The imaging condition includes the body part to be imaged, the tube voltage, the tube current, and the irradiation stop threshold value. As described above, the irradiation stop threshold value is information for determining whether or not to stop the X-ray irradiation by being compared with the accumulated dose in the large block 75 defined as the dose measurement field by the AEC section 60.

The console 14 reads out the imaging condition corresponding to the command inputted by the operator from the imaging condition table 70. The console 14 transmits the imaging condition thus read out to the electronic cassette 13. The electronic cassette 13 receives the imaging condition through the communication I/F 55, and inputs the received imaging condition to the control section 48. The control section 48 provides the AEC section 60 with the irradiation stop threshold value included in the imaging condition.

Figure 6:
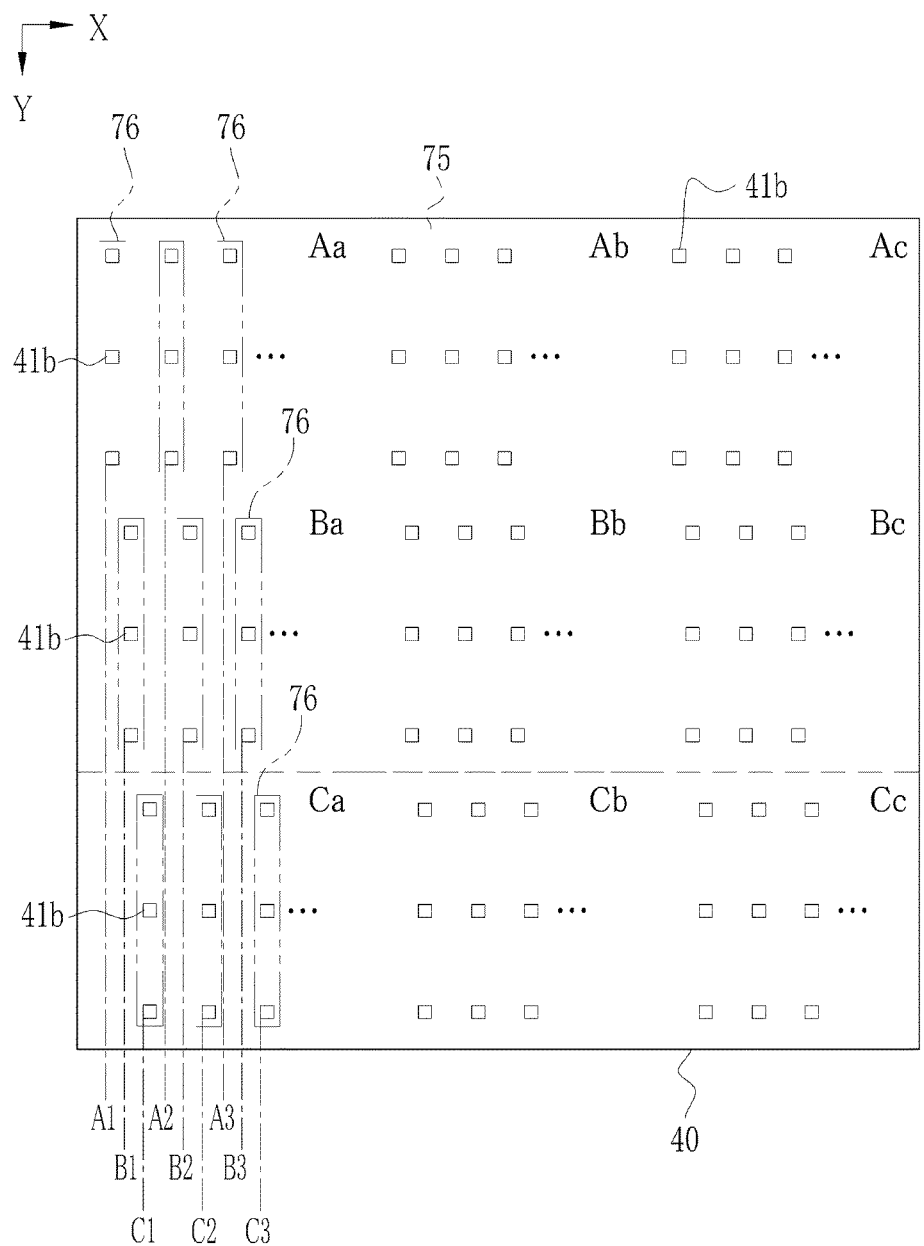
FIG. 6 is a view showing arrangement of large blocks and small blocks.

As shown in FIG. 6, the imaging area 40 is equally divided into nine square-shaped large blocks 75 arranged in three rows and three columns. As exemplified by each of the large blocks 75 in the leftmost column, a plurality of the small blocks 76 exist in each of the large blocks 75. A plurality of the detection pixels 41b in each of the small blocks 76 (the number of the small blocks 76 is three in this embodiment) are connected to a single one of the signal lines 45. The small blocks 76 are arranged so as not to be overlapped with each other in the Y direction.

In the case where the small blocks 76 are not overlapped with each other in the Y direction, more concretely, it means that the detection pixels 41b in each of the small blocks 76 are arranged so as not to be overlapped with the detection pixels 41b in other small blocks 76 in the Y direction. Dashed lines assigned with reference numerals A1 to A3, B1 to B3, and C1 to C3 are straight lines drawn from the detection pixels 41b in the respective small blocks 76 in order to represent that the small blocks 76 are not overlapped with each other in the Y direction, for descriptive purposes. Each of the reference numerals A1 to A3 denotes a straight line drawn from each of the small blocks 76 in the large block 75 assigned with a reference numeral Aa. Similarly, each of the reference numerals B1 to B3 denotes a straight line drawn from each of the small blocks 76 in the large block 75 assigned with a reference numeral Ba, and each of the reference numerals C1 to C3 denotes a straight line drawn from each of the small blocks 76 in the large block 75 assigned with a reference numeral Ca. The dashed lines assigned with the reference numerals A1 to A3, B1 to B3, and C1 to C3 are not overlapped with each other in the Y direction. Note that, the same holds true for the small blocks 76 in the large blocks 75 assigned with reference numerals Ab, Ac, Bb, Bc, Cb, and Cc.

In the case where the small blocks 76 are not overlapped with each other in the Y direction, from the view point of the structure, it means that only one small block 76 is provided to a single one of the signal lines 45. Therefore, in the case where the pixels 41 are arranged in a matrix in the imaging area 40 as shown in FIG. 4, the detection pixels 41b contained in each of the small blocks 76 are deviated from the detection pixels 41b contained in other small blocks 76 with a deviation degree corresponding to at least one column of pixels. The rule that the small blocks 76 are arranged so as not to be overlapped with each other in the Y direction is also applied to the inside of one large block 75, and three large blocks 75 adjacent to each other in the Y direction (namely, the combination of Aa, Ba, and Ca, the combination of Ab, Bb, and Cb, and the combination of Ac, Bc, and Cc). Further, the small blocks 76 are arranged so as to be aligned in the X direction among three large blocks 75 adjacent to each other in the X direction (namely, the combination of Aa, Ab, and Ac, the combination of Ba, Bb, and Bc, and the combination of Ca, Cb, and Cc).

Figure 7:
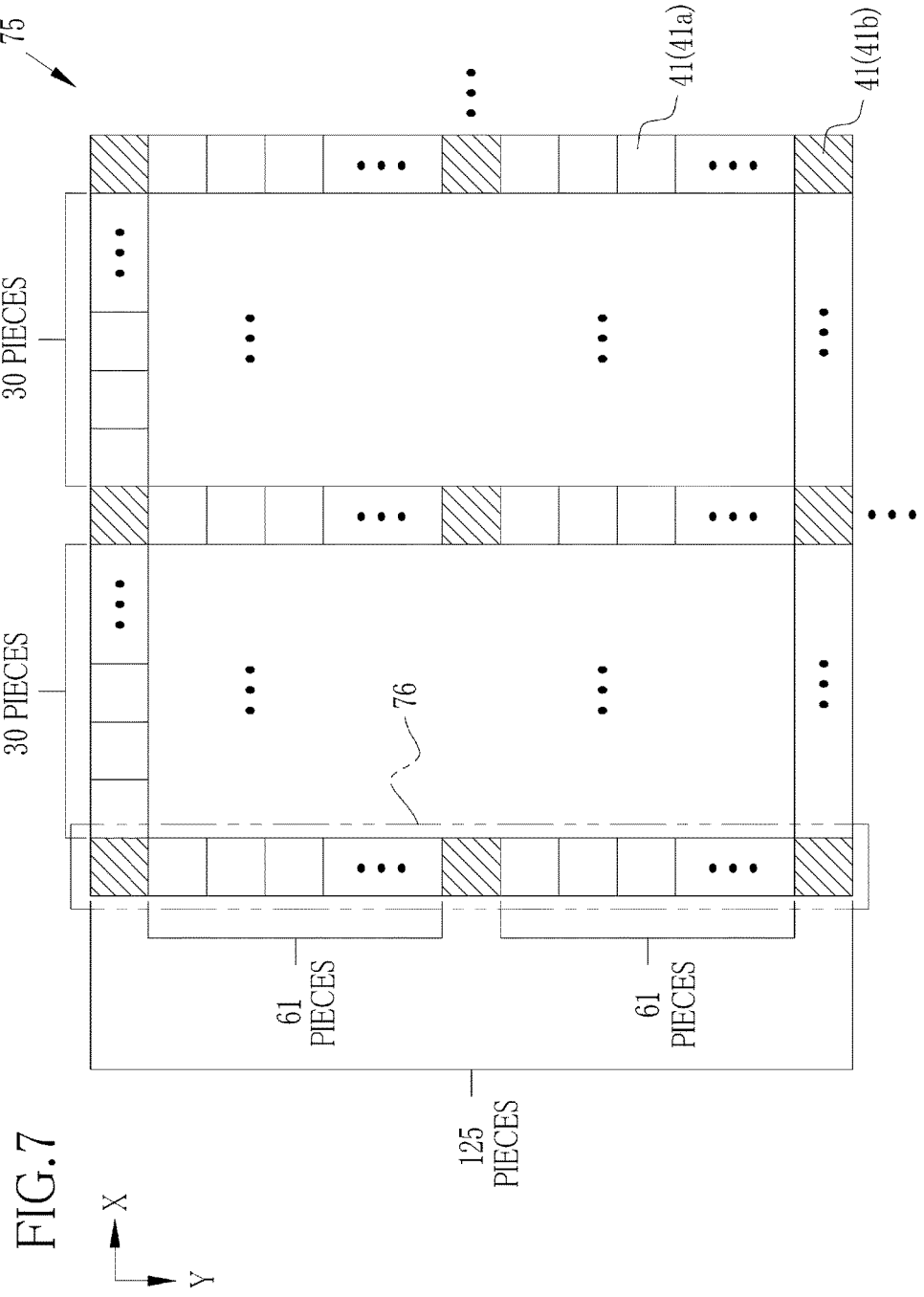
FIG. 7 is an enlarged view showing a structure of the small block and arrangement of the small blocks.

As shown in FIG. 7, each of the small blocks 76 consists of 125 pieces of the pixels 41 aligned in the Y direction, for example, in which 3 pieces of the detection pixels 41b are disposed such that 61 pieces of the normal pixels 41a are sandwiched between one of the detection pixels 41b. Further, the small block 76 is disposed for every 30 columns in each of the large blocks 75, for example. (Namely, one small block 76 is contained for every 30 columns.) As shown in FIG. 6, in the large block 75 assigned with the reference numeral Aa, the small block 76 located at the leftmost column is considered as the first column, and the small block 76 is disposed at 1st, 31th, 61th, 91th columns, for example. The same holds true for the large blocks 75 assigned with the reference numerals Ab and Ac which are aligned with the large block assigned with the reference numeral Aa in the X direction. Further, the small block 76 is disposed at 11th, 41th, 71th, 101th, columns in the large blocks 75 assigned with the reference numerals Ba, Bb, and Bc. Furthermore, the small block 76 is disposed at 21th, 51th, 81th, 111th, columns in the large blocks 75 assigned with the reference numerals Ca, Cb, and Cc. Therefore, in 3 pieces of the large blocks 75 adjacent to each other in the Y direction, as a whole, the small block 76 is disposed at 1st, 11th, 21th, 31th, 41th, 51th, . . . , 91th, 101th, 111th, . . . columns, namely, for every 10 columns. (Namely, one small block 76 is contained for every 10 columns.)

Specifically, the small block 76 in each of the large blocks 75 has a structure in which 3 pieces of the detection pixels 41b are disposed such that 61 pieces of the normal pixels 41a are sandwiched between one of the detection pixels 41b in the Y direction as shown in FIG. 7, and the small block 76 is disposed for every 30 columns as shown in FIG. 6, such that the same arrangement pattern is achieved. However, the small block 76 is disposed for every 10 columns such that the arrangement pattern of the small blocks 76 is deviated with a deviation degree corresponding to at least one signal line 45 (one column of pixels) between the large blocks 75 adjacent to each other in the Y direction.

Next, one sequence of X-ray imaging operation with use of the X-ray imaging system 2 is described hereinbelow. At first, the object is set to a predetermined imaging position on one of the upright-posture imaging table 15 and the supine-posture imaging table 16. Positioning is performed by adjusting a height and a horizontal position of the electronic cassette 13 to the body part of the object to be imaged. Then, a height and a horizontal position of the X-ray source 10, and a size of the irradiation field of the X-rays from the X-ray source 10 are adjusted in accordance with the position of the electronic cassette 13 and the size of the body part to be imaged. Next, the imaging condition is set for the source controller 11 and the console 14. The imaging condition set for the console 14 is provided to the electronic cassette 13.

After the preparation for the X-ray imaging is completed, the operator presses the irradiation switch 12 halfway. Upon the halfway pressing of the irradiation switch 12, the source controller 11 issues the warm-up start signal to the high-voltage generator 20 to start the warming-up of the X-ray source 10. After the halfway pressing of the irradiation switch 12, the operator fully presses the irradiation switch 12 while monitoring the time required for the warming-up of the X-ray source 10. Upon the full pressing of the irradiation switch 12, the source controller 11 transmits the irradiation start request signal to the electronic cassette 13.

In a standby mode before the X-ray imaging, the sensor panel 30 of the electronic cassette 13 repeats the reset operation and waits for the irradiation start request signal. Upon receiving the irradiation start request signal from the source controller 11, the sensor panel 30 checks a state of the electronic cassette 13, and transmits the irradiation permission signal to the source controller 11. Concurrently, the sensor panel 30 finishes the reset operation and starts the accumulation operation and the dose detection operation, in other words, shifts from the standby mode to an imaging mode.

Upon receiving the irradiation permission signal from the sensor panel 30, the source controller 11 issues the irradiation start signal to the high-voltage generator 20 so as to start X-ray irradiation from the X-ray source 10. The X-rays irradiated from the X-ray source 10 pass through the object and enter the sensor panel 30.

In the dose detection operation, the electric charges generated in the detection pixels 41*b* are read out at a predetermined sampling rate repeatedly in the sensor panel 30. Based on the dose signals read out at a predetermined sampling rate and transmitted from the detection pixels 41*b*, the AEC section 60 calculates the accumulated dose of each of large blocks 75, and designates the large block 75 which exhibits the minimum accumulated dose as the dose measurement field. The AEC section 60 compares the accumulated dose in the dose measurement field with the irradiation stop threshold value so as to determine whether or not the accumulated dose has reached the irradiation stop threshold value.

When it is determined that the accumulated dose in the dose measurement field has reached the irradiation stop threshold value, the AEC section 60 issues the irradiation stop signal. The irradiation stop signal is transmitted to the source controller 11. Upon receiving the irradiation stop signal, the source controller 11 stops the X-ray irradiation from the X-ray source 10.

After the transmission of the irradiation permission signal, in the sensor panel 30, the accumulation operation in the normal pixels 41*a* is performed. When it is determined that the accumulated dose in the dose measurement field has reached the irradiation stop threshold value and the irradiation stop signal is transmitted by the AEC section 60, the operation of the sensor panel 30 shifts from the accumulation operation to the readout operation. Thereby, the image data representing the X-ray image of the single frame is outputted to the memory 54. After the readout operation, the sensor panel 30 returns to the standby mode for performing the reset operation.

The various image processing circuits of the control section 48 apply various types of image processing to the X-ray image outputted to the memory 54 in the readout operation. The X-ray image after the image processing is transmitted to the console 14, and is displayed on the monitor 14*b*, for use in diagnosis. Thereby, one sequence of X-ray imaging operation is completed.

Since the small blocks 76 are arranged so as not to be overlapped with each other in the Y direction in each of the large blocks 75 obtained by equally dividing the imaging area 40 in X and Y directions, detailed two-dimensional information of the accumulated dose all over the imaging area 40 can be obtained, and thereby AEC can be performed more accurately.

Note that, the number of pixels constituting the small block (i.e. the size of the small block), the number of the detection pixels contained in each of the small blocks, and the interval of the columns for the arrangement of the small blocks are not limited to the exemplification in the above embodiment, and may be arbitrarily changed. Alternatively, they may be changed for each of the large blocks.

Figure 8:
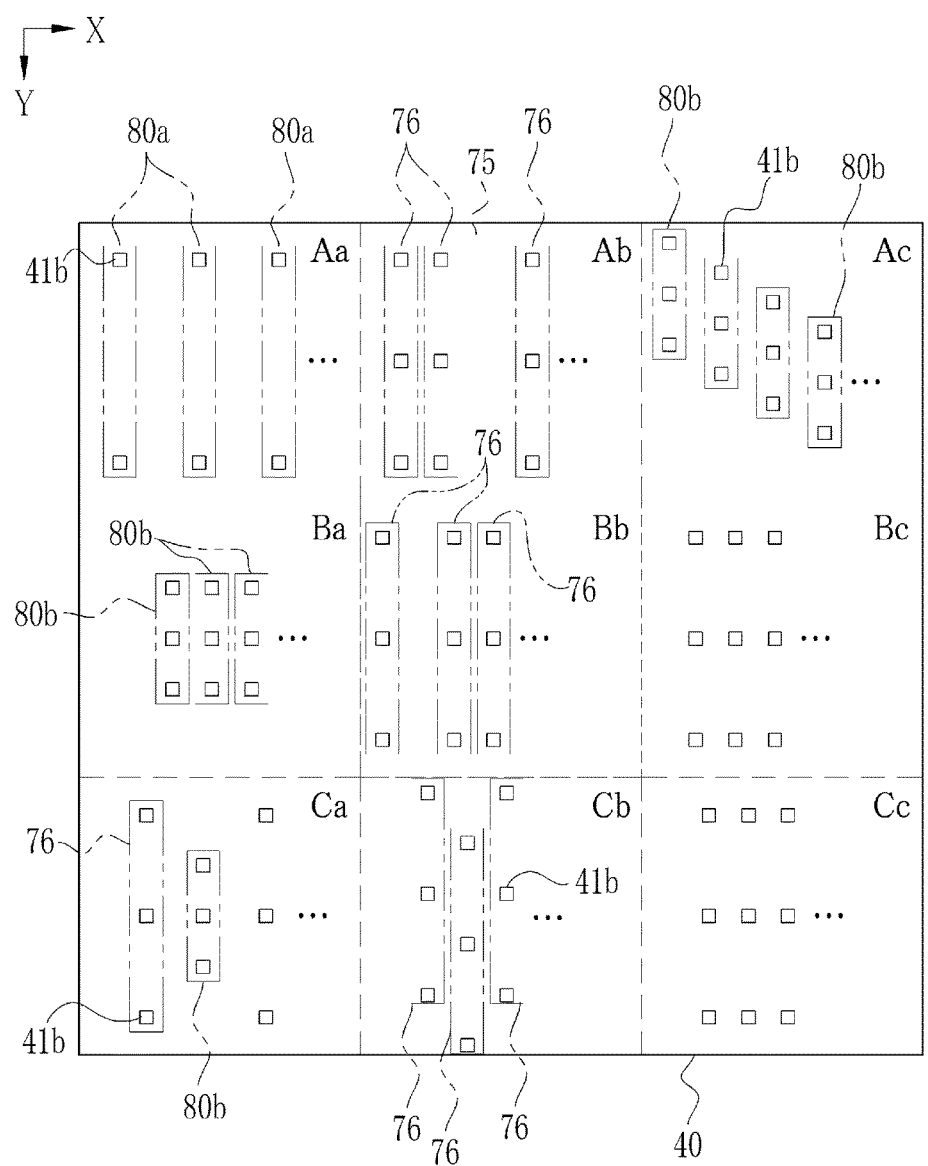
FIG. 8 is a view showing a structure of the small block and arrangement of the small blocks according to another embodiment.

FIG. 8 shows an example in which the number of pixels constituting the small block (i.e. the size of the small block), the number of the detection pixels contained in each of the small blocks, and the interval of columns for the arrangement of the small blocks are changed. In FIG. 8, the small block 80*a* disposed in the large block 75 assigned with the reference numeral Aa consists of 125 pieces of the pixels 41 aligned in the Y direction in the same manner as the above embodiment. However, the small block 80*a* consists of 2 pieces of the detection pixels 41*b* and 123 pieces of the normal pixels 41*a* sandwiched between the detection pixels 41*b*, and is disposed for every 60 columns which is twice as that in the above embodiment. In comparison with the above embodiment, the number the detection pixels 41*b* is smaller, and arrangement density thereof is coarser in the large block 75. On the other hand, the small block 80*b* disposed in the large block 75 assigned with the reference numeral Ba includes 3 pieces of the detection pixels 41*b* in the same manner as the above embodiment. However, the distance between the detection pixels 41*b* is narrow, and the small blocks 80*b* are densely disposed in a central portion of the large block 75. Furthermore, in the large block 75 assigned with the reference numeral Ca located under the large block 75 assigned with the reference numeral Ba, the small blocks 76 having the same structure as that in the above embodiment and the small blocks 80*b* having the same structure as that in the large block 75 assigned with the reference numeral Ba are arranged in a mixed state.

In each of the large block 75 assigned with the reference numeral Ab and the large block 75 assigned with the reference numeral Bb, the interval of columns for the arrangement of the small blocks 76 varies, and there are portions in which the density of the detection pixels 41*b* is coarse and portions in which the density of the detection pixels 41*b* is dense in a mixed state. Further, in the large block 75 assigned with the reference numeral Cb, the small blocks 76 are deviated from each other in the Y direction such that the detection pixels 41*b* are disposed in a staggered arrangement. Furthermore, in the large block 75 assigned with the reference numeral Ac, along a diagonal line connecting the upper left corner and the lower right corner of the large block 75, the positions of the small blocks 80*b* are serially deviated in the X direction.

As described above, the structure and arrangement of the small blocks may be varied as long as the rule that each of the small blocks is disposed so as not to straddle the large blocks adjacent to each other (namely, all the plural detection pixels 41*b* contained in one small block exist within one large block) and the small blocks are disposed so as not to be overlapped with each other in the Y direction is satisfied. However, from the view point of manufacturability of the sensor panel, it is preferable that the small blocks 76 are periodically disposed so as to achieve the same arrangement pattern in all the large blocks 75 as shown in FIG. 6, since the production of the sensor panel is facilitated in comparison the case where the small blocks each having a different structure are disposed in the large block 75 as with the large block 75 assigned with the reference numeral Ca in FIG. 8 or the case where the interval of columns for the arrangement of the small blocks varies in the large block 75 as with the large block 75 assigned with the reference numeral Ab or Bb in FIG. 8.

Moreover, it is more preferable that the detection pixels 41*b* are aligned in the X direction as shown in FIG. 6 in comparison with the case where the detection pixels 41*b* are not aligned in the X direction in the large block 75 as with the large block 75 assigned with the reference numerals Cb or Ac in FIG. 8, from the view point of manufacturability.

In the case where the detection pixels 41*b* are densely disposed in the large block 75 as with the large block 75 assigned with the reference numeral Ba in FIG. 8, it is possible to detect the accumulated dose particularly in the portion on which the detection pixels 41*b* are disposed. In contrast, in the case where the detection pixels 41*b* are evenly disposed in the large block 75 as shown in FIG. 6, it is possible to obtain information reflecting the accumulated dose of the entire area in the large block 75. Note that, although the detection pixels 41*b* are densely disposed in the central portion of the large block 75 assigned with the reference numeral Ba in FIG. 8, the portion for disposing the detection pixels 41*b* is not limited to the central portion of the large block 75. In the case where a particular portion of a certain large block tends to be selected as the dose measurement field (such as left and right lung fields in chest radiography and chest wall in breast radiography, for example), the detection pixels 41*b* may be centralized in the particular portion.

Figure 9:
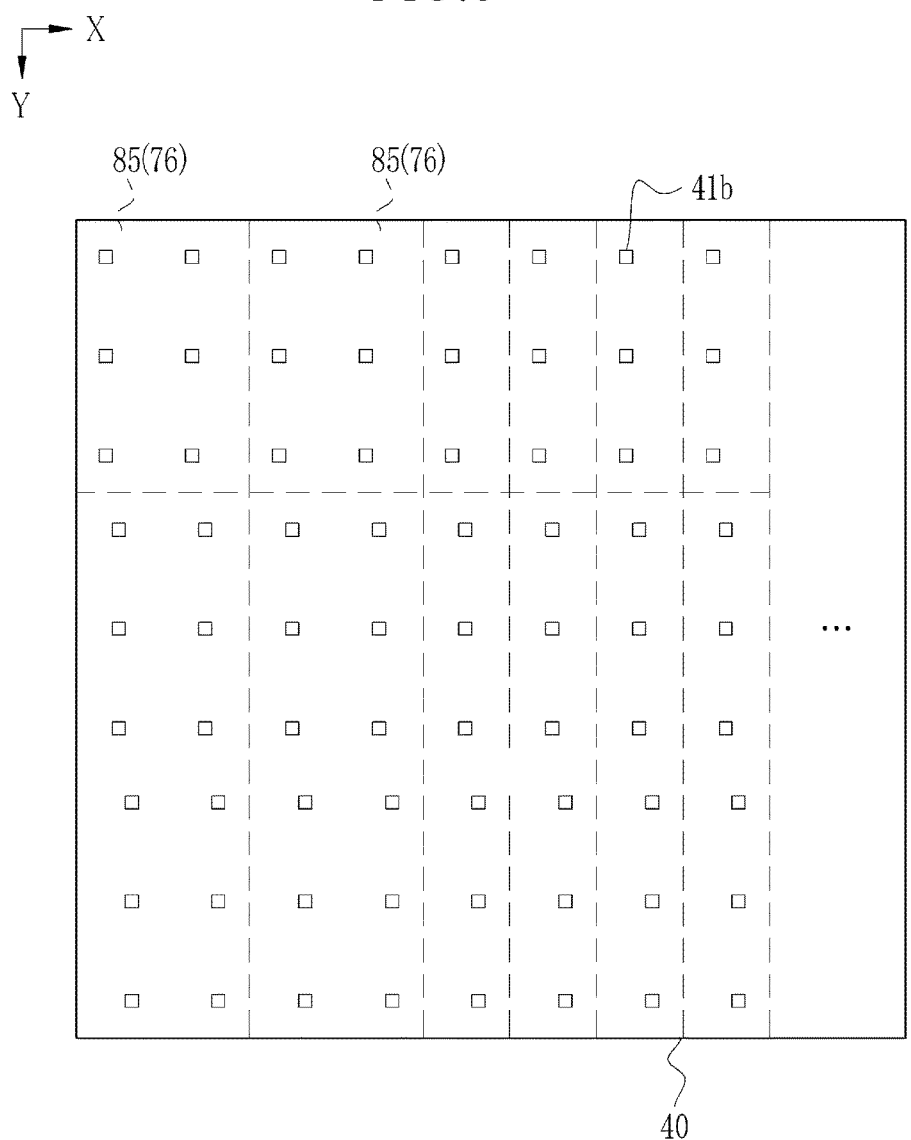
FIG. 9 is a view showing large blocks each having a rectangular shape.

FIG. 9 shows an example of a large block 85 having a rectangular shape. One small block 76 of the above embodiment is disposed on the large block 85. Namely, the large block 85 equivalents to the small block 76 itself. Accordingly, the number of the large blocks is not limited to 9 consisting of three rows and three columns unlike the above embodiment. Further, the shape of the large block is not limited to the square shape unlike the above embodiment. Furthermore, the number of the small blocks disposed in the large block may be one instead of two or more.

Although the TFT 43 of the detection pixel 41*b* has a short between the source electrode and the drain electrode in the above embodiment, a pixel in which the photoelectric converter 42 is directly connected to the signal line 45 without intermediation of the TFT 43 may be used as the detection pixel. Additionally, a detection pixel 41*c* shown in FIG. 10 may be used. Note that, the same components as those in the above embodiment are denoted by the same reference numerals respectively, and the explanation thereof will be omitted.

Figure 10:
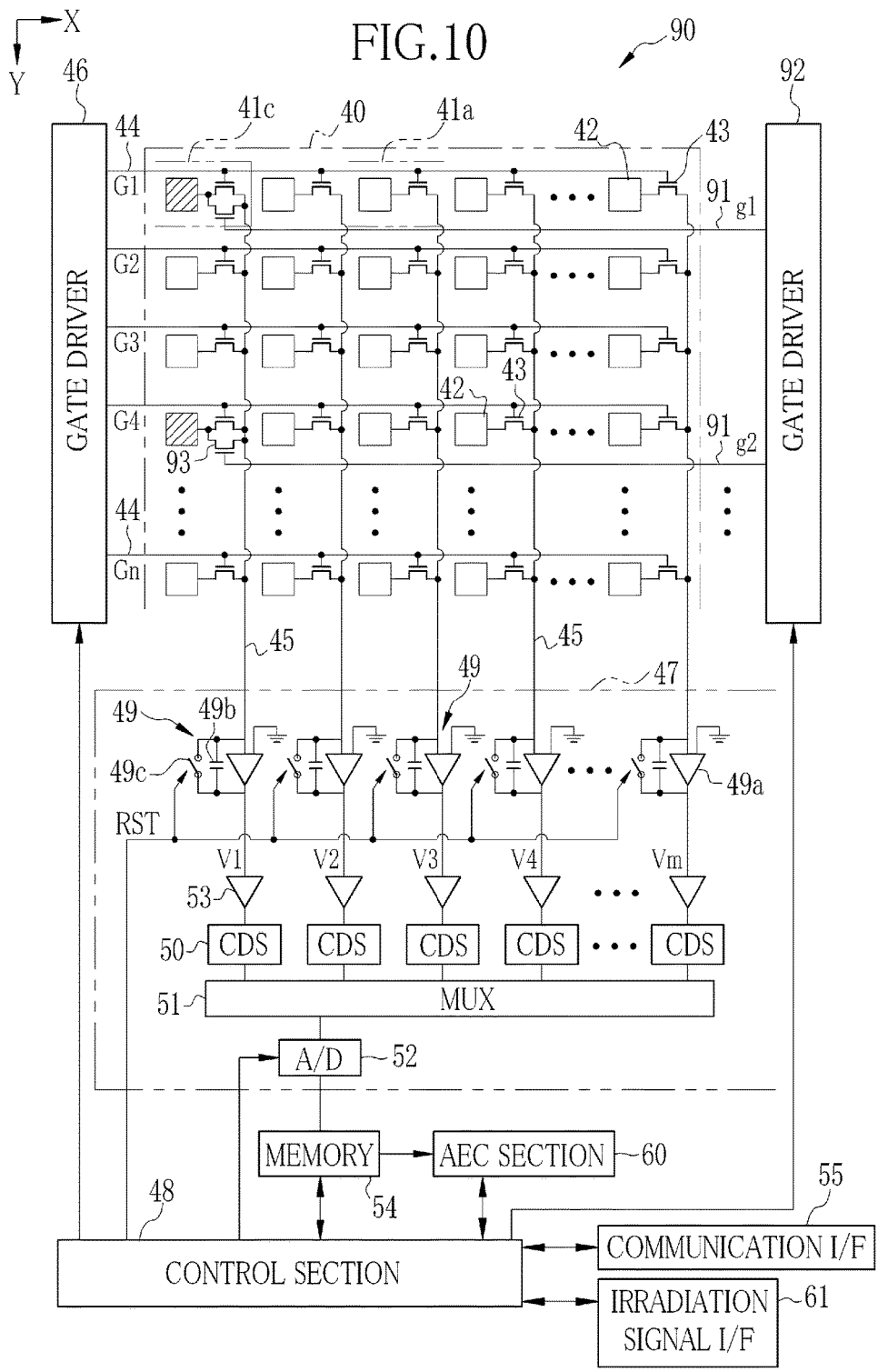
FIG. 10 is a block diagram showing an internal structure of an electronic cassette according to another embodiment.

As shown in FIG. 10, a sensor panel 90 has detection pixels 41*c* each of which is connected to a TFT 93 driven by a scanning line 91 and a gate driver 92, while the scanning line 91 and the gate driver 92 are respectively different from the scanning line 44 and the gate driver 46 for driving the TFT 43 of the normal pixel 41*a*. Since each of the detection pixels 41*c* is connected to the TFT 93, the electric charges can be read out from the detection pixel 41*c* even if the TFTs 43 of the normal pixels 41*a* in the same row are turned off and the charge accumulation operation is performed.

In the dose detection operation, under the control of the control section 48, the gate driver 92 sequentially issues gate pulses g1, g2, g3, . . . , and gk (k<n) at a predetermined time interval so as to drive the TFTs 93 in the same row at a time. Thereby, the scanning lines 91 are sequentially activated one by one, and the TFTs 93 connected to the scanning lines 91 are turned on sequentially on a row-by-row basis. The time period for which the TFTs 93 are in an ON state is defined by a pulse width of the gate pulse. Upon elapse of the time period defined by the pulse width, the TFTs 93 return to an OFF state. The electric charges generated in the photoelectric converter 42 of each of the detection pixels 41*c* flow into the capacitor 49*b* of the integration amplifier 49 through the signal line 45 while the TFT 93 is in an ON state, irrespective of whether the TFT 43 is turned on or turned off. The electric charges accumulated in the integration amplifier 49 is transmitted from the detection pixel 41*c* to the A/D 52, and converted into a dose signal by the A/D 52. The subsequent processing is the same as that in the above embodiment, and therefore the explanation thereof will be omitted.

In the case of the sensor panel 90, as long as the detection pixels 41*b* are aligned in the X direction as shown in FIG. 6, it is sufficient to wire one scanning line 91 for the detection pixels 41*b* aligned in the X direction, and therefore it becomes possible to simplify the wiring of the scanning line 91.

Note that, in the sensor panel 90, while the TFT 93*s* are turned off, the detection pixels 41*c* can be used as the normal pixels 41*a*. Accordingly, a lot of the detection pixels 41*c* may be disposed, such that the number of the pixels for constituting the small block (i.e. the size of the small block), the number of detection pixels to be contained in each of the small blocks, and the arrangement of the small blocks may become variable in accordance with the body part to be imaged or the body frame of the object. For example, in the case where the body part to be imaged is thick and has a relatively large area, such as the case of chest and abdomen, the size of each of the small blocks is made large, and the number of the detection pixels contained in each of the small blocks is increased. In contrast, in the case where the body part to be imaged is thin and has a relatively small area, such as the case of hand or finger, the size of each of the small blocks is made small, and the number of the detection pixels contained in each of the small blocks is decreased.

In the above embodiments, as shown in FIGS. 4 and 10, the normal pixel 41*a*, the detection pixel 41*b*, and the detection pixel 41*c* are connected to the same signal line 45. Since each of the detection pixels 41*b* and 41*c* is regarded as a defect pixel, the number of the detection pixels 41*b* and 41*c* is preferably small. Further, since only one small block is disposed on a column-by-column basis, the number of the detection pixels is much smaller than the number of the normal pixels in the column having the small block. Even while the TFTs are turned off, a slight amount of leak current flows from the normal pixels to the signal line. The number of the normal pixels is much larger than the number of the detection pixels, and therefore in accordance with the number of the normal pixels, the electric charges based on the leak current from the normal pixels are unnecessarily added to the electric charges from the detection pixels to be used as the base of the dose signal. Consequently, there is a problem that the electric charges based on the leak current from the normal pixels prominently affect as noise components on the dose signal.

Figure 11:
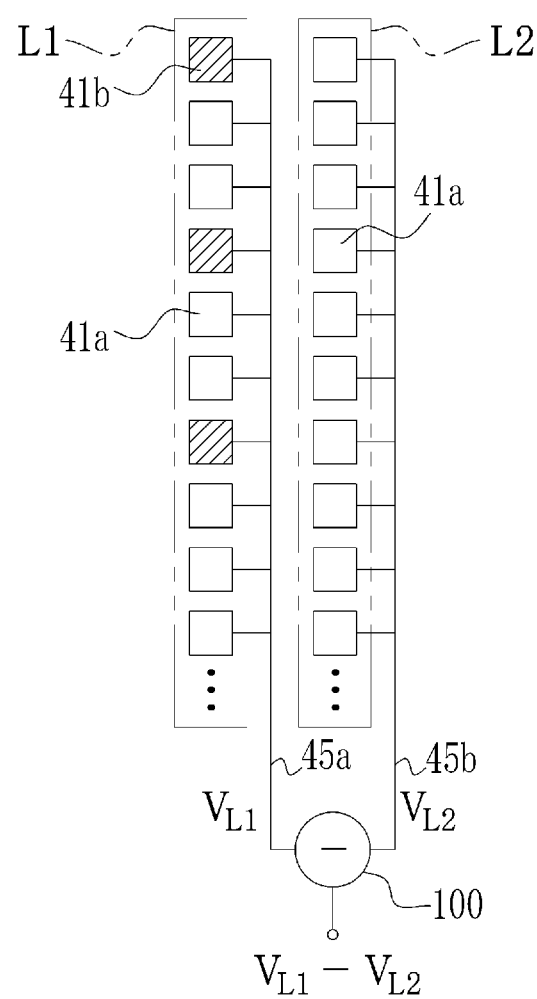
FIG. 11 is a view of a subtraction circuit for subtracting a voltage signal in a column having no small blocks from a voltage signal in a column having the small blocks.
Figure 12:
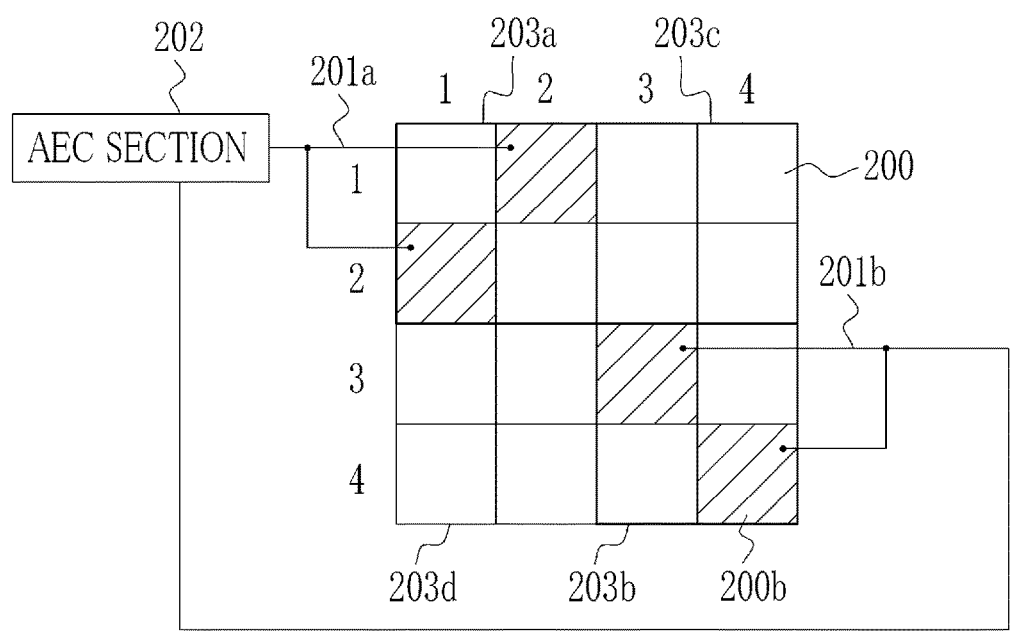
FIG. 12 is a view showing arrangement of detection pixels in a conventional manner.

Hence, as schematically shown in FIG. 11, there are disposed a column L1 having small blocks (detection pixels) and connected to a signal line 45*a* (e.g. the column for outputting the voltage signal V1 in FIGS. 4 and 10), and a column L2 having no small blocks and connected to a signal line 45*b* (e.g. the column for outputting the voltage signal V2 in FIGS. 4 and 10), in a state that the column L2 is adjacent to the column L1. At the time of sampling of the dose signal in the AEC section 60, it is preferable that a voltage signal $V_{L2}$ of the column L2 is subtracted from a voltage signal $V_{L1}$ of the column L1 in a subtraction circuit 100 so as to remove the affect on the electric charges based on the leak current from the normal pixels from the voltage signal $V_{L1}$ of the column L1 and extract only the output based on the electric charges from the detection pixels. It is because the number of the pixels is the same in each of the columns that the leak current component can be removed from the voltage signal $V_{L1}$ by subtracting the voltage signal $V_{L2}$ from the voltage signal $V_{L1}$. Accordingly, it is preferable that two or more columns L2 sandwich one column L1, such as the case where the small block is disposed for every 10 columns as with the above embodiment, rather than the case where the small block is disposed in each of the columns such that every column equivalents to the column L1 having the small block. Note that, as the arrangement of the pixels, in addition to the matrix of pixels in the above embodiment, there may be a honeycomb arrangement in which the pixels are tilted by 45°. In the honeycomb arrangement, since the number of the pixels connected to one signal line is the same or substantially the same between the adjacent columns, it is also possible to remove the leak current component from the voltage signal of the signal line to which the small blocks are connected.

In FIG. 4, the TFT 43 of the detection pixel 41 has a short between the source electrode and the drain electrode, and therefore, it is impossible to prevent the electric charges generated in the photoelectric converter 42 of the detection pixel 41b from flowing into the capacitor 49b. However, in the case of the detection pixels 41b shown in FIG. 10, as long as the TFTs 43 and 93 are turned off, the generated electric charges do not flow into the capacitors 49b. Accordingly, in the sensor panel 90 in FIG. 10, while the TFTs 43 and 93 are turned off, the column L1 behaves as if it is the column L2. Therefore, in this case, while the TFTs 43 and 93 are turned off, the sampled voltage signal is substituted with the voltage signal $V_{L2}$ of the column L2, and then while the TFT 43 is turned off and the TFT 93 is turned on, the voltage signal $V_{L2}$ is subtracted from the voltage signal $V_{L1}$ outputted from the column L1. Namely, it is not necessary to dispose the column L2 to be adjacent to the column L1.

Note that, in FIG. 11, there is one column L1 and one column L2. However, alternatively, two or more columns L2 may be used for one column L1 so as to remove the affect of the electric charges based on the leak current from the normal pixels from the voltage signal $V_{L1}$. In this case, the voltage signals $V_{L2}$ of two or more columns L2 (e.g. one or two columns L2 disposed at each side of the column L1 in the X direction) are integrated, and then the resultant value is divided by the number of the columns L2, so as to calculate an average value of the voltage signals $V_{L2}$. Thereafter, the average value is subtracted from the voltage signal $V_{L1}$ of the column L1 in the subtraction circuit 100. Accordingly, even in the case where the value of the voltage signal $V_{L2}$ varies depending the columns L2, the variation is averaged, and therefore it is possible to extract only the output based on the electric charges from the detection pixels more accurately. In particular, in the case of detecting uneven dose in the imaging area, namely, the dose having passed through the object, the leak current from each of the columns is not always the same, and therefore it is effective to average the voltage signals $V_{L2}$ of two or more columns L2. Further, in the case where the number of the columns L2 is one, if there is line defect in the column L2, it becomes impossible to extract only the output based on the electric charges from the detection pixels correctly from the column L1. However, in the case where two or more columns L2 are prepared, even if there is line defect in one of the columns L2, the voltage signal $V_{L2}$ of the remaining columns L2 may be used to correct the voltage signal $V_{L1}$.

In the above embodiments, there is shown an example in which one normal detection pixel is inevitably used as the detection pixel. However, the present invention is not limited to this example. For example, a sub-pixel, which is obtained by separating part of the photoelectric converter in one pixel, may be used as the detection pixel. Alternatively, a dedicated detection pixel may be disposed at a space between the pixels. However, in any cases, the same signal line is used for one column as with the above embodiments.

In the above embodiments, when the accumulated dose of the X-rays has reached the irradiation stop threshold value during the X-ray imaging, the irradiation stop signal is outputted. However, the time at which the accumulated dose of X-rays reaches the irradiation stop threshold value may be predicted based on the integrated value of the dose signals, and the irradiation stop signal may be transmitted to the source controller at the moment of reaching the predicted time, or information of the predicted time itself may be transmitted to the source controller. In the latter case, the source controller measures the irradiation time, and stops the X-ray irradiation at the moment when the irradiation time reaches the predicted time.

Although the console 14 and the electronic cassette 13 are separated from each other in the above embodiments, the console 14 may not be necessarily independent of the electronic cassette 13. The functions of the console 14 may be installed into the electronic cassette 13. Further, the console 14 may have part of the functions of the electronic cassette 13. Furthermore, in addition to the electronic cassette 13 and the console 14, an imaging control device for executing part of the functions of the console 14 for controlling the electronic cassette 13 may be provided.

In the above embodiments, the sensor panel is the TFT type. However, the sensor panel can be a CMOS type. Further, the present invention is applicable to not only an electronic cassette as a portable X-ray image detecting device but also an X-ray image detecting device installed on an imaging table. Furthermore, the present invention is applicable not only the case of imaging X-rays but also the case of imaging radiation such as gamma rays.

Although the present invention has been fully described by the way of the preferred embodiment thereof with reference to the accompanying drawings, various changes and modifications will be apparent to those having skill in this field. Therefore, unless otherwise these changes and modifications depart from the scope of the present invention, they should be construed as included therein.

What is claimed is:

1. An X-ray radiation image detecting device including a sensor panel having an imaging area provided with pixels, each pixel for accumulating electric charges corresponding to a dose of X-ray radiation having passed through an object and outputting the accumulated electric charges to a signal line, the X-ray radiation image detecting device performing automatic exposure control, in which part of the pixels are used as detection pixels for detecting the X-ray radiation dose, wherein it is determined whether or not an accumulated dose has reached a target dose based on the output of the detection pixels through the signal lines, and wherein X-ray radiation irradiation is stopped when it is determined that the accumulated dose has reached the target dose, the X-ray radiation image detecting device comprising:
- a plurality of large blocks obtained by dividing the imaging area in a first direction along the signal lines and a second direction orthogonal to the first direction; and
- at least one small block disposed in each of the large blocks, the small block consisting of a plurality of the detection pixels connected to a single one of the signal lines, wherein the small blocks are arranged so as not to be overlapped with each other in the first direction, wherein:

the pixels include the detection pixels and normal pixels different from the detection pixels, each of the normal pixels accumulates the electric charges and outputs the electric charges to the signal line upon turning off and on of a first switching element, and the electric charges generated in each of the detection pixels flow into the signal line irrespective of whether the first switching element is turned on or turned off, the X-ray radiation image detecting device further comprising:
- a subtraction device for subtracting a voltage signal outputted from the signal line not being provided with the small blocks in a state that the first switching element is turned off from a voltage signal outputted from the signal line being provided with the small blocks in a state that the first switching element is turned off, wherein the automatic exposure control is performed based on the voltage signal obtained by the subtraction by the subtraction device, and the small blocks are arranged with an interval corresponding to at least one of the signal lines therebetween, such that the signal line not being provided with the small blocks is adjacent to the signal line being provided with the small blocks.

2. The X-ray radiation image detecting device according to claim 1, wherein the subtraction device samples the voltage signals outputted from a plurality of the signal lines each of which is not provided with the small blocks.

3. An X-ray radiation image detecting device including a sensor panel having an imaging area provided with pixels, each pixel for accumulating electric charges corresponding to a dose of X-ray radiation having passed through an object and outputting the accumulated electric charges to a signal line, the X-ray radiation image detecting device performing automatic exposure control, in which part of the pixels are used as detection pixels for detecting the X-ray radiation dose, wherein it is determined whether or not an accumulated dose has reached a target dose based on the output of the detection pixels through the signal lines, and wherein X-ray radiation irradiation is stopped when it is determined that the accumulated dose has reached the target dose, the X-ray radiation image detecting device comprising:
- a plurality of large blocks obtained by dividing the imaging area in a first direction along the signal lines and a second direction orthogonal to the first direction; and
- at least one small block disposed in each of the large blocks, the small block consisting of a plurality of the detection pixels connected to a single one of the signal lines, wherein the small blocks are arranged so as not to be overlapped with each other in the first direction, wherein the pixels include the detection pixels and normal pixels different from the detection pixels, each of the normal pixels accumulates the electric charges and outputs the electric charges to the signal line upon turning off and on of a first switching element, and each of the detection pixels is provided with a second switching element in addition to the first switching element, and the electric charges generated in each of the detection pixels flow into the signal line upon turning on of the second switching element irrespective of whether the first switching element is turned on or turned off.

4. The X-ray radiation image detecting device according to claim 3, further comprising:
- a subtraction device for subtracting a voltage signal outputted from the signal line being provided with the small blocks in a state that the first and second switching elements are turned off from a voltage signal outputted from the same signal line in a state that the first switching element is turned off and the second switching element is turned on, wherein the automatic exposure control is performed based on the voltage signal obtained by the subtraction by the subtraction device.

* * * * *